(12) United States Patent
Sood et al.

(10) Patent No.: US 7,244,566 B2
(45) Date of Patent: Jul. 17, 2007

(54) ANALYTE DETECTION

(75) Inventors: Anup Sood, Flemington, NJ (US); Shiv Kumar, Belle Mead, NJ (US); Carl Fuller, Berkeley Heights, NJ (US); John Nelson, Hillsborough, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 471 days.

(21) Appl. No.: 10/651,582

(22) Filed: Aug. 29, 2003

(65) Prior Publication Data

US 2004/0224319 A1 Nov. 11, 2004

Related U.S. Application Data

(63) Continuation-in-part of application No. 10/113,030, filed on Apr. 1, 2002, now Pat. No. 7,052,839, and a continuation-in-part of application No. 10/113,025, filed on Apr. 1, 2002, now Pat. No. 7,033,762.

(60) Provisional application No. 60/406,892, filed on Aug. 29, 2002, provisional application No. 60/406,893, filed on Aug. 29, 2002, provisional application No. 60/406,894, filed on Aug. 29, 2002, provisional application No. 60/315,798, filed on Aug. 29, 2001.

(51) Int. Cl.
*C12Q 1/68* (2006.01)
(52) U.S. Cl. .......................................................... 435/6
(58) Field of Classification Search ..................... None
See application file for complete search history.

(56) References Cited

U.S. PATENT DOCUMENTS

| 5,565,323 | A | * | 10/1996 | Parker et al. .................. | 435/6 |
| 5,702,925 | A | | 12/1997 | Smith et al. | |
| 5,843,634 | A | | 12/1998 | Brate et al. | |
| 5,872,243 | A | | 2/1999 | Gee et al. | |
| 5,986,076 | A | * | 11/1999 | Rothschild et al. ......... | 536/22.1 |
| 6,001,571 | A | * | 12/1999 | Mandecki ...................... | 435/6 |
| 6,255,083 | B1 | * | 7/2001 | Williams ...................... | 435/91.1 |
| 6,403,339 | B1 | | 6/2002 | Bertling | |
| 6,600,028 | B1 | | 7/2003 | Brown et al. | |
| 6,936,702 | B2 | * | 8/2005 | Williams et al. ........... | 536/22.1 |
| 2003/0096253 | A1 | | 5/2003 | Nelson et al. | |
| 2003/0124576 | A1 | | 7/2003 | Kumar et al. | |

FOREIGN PATENT DOCUMENTS

WO WO03/020984 3/2003

OTHER PUBLICATIONS

Newton, C. R., et al. "The Production of PCR Products with 5' Single-Stranded Tails Using Primers that Incorporate Novel Phosphoramidite Intermediates" Nucleic Acid Research, Oxford University Press, Surrey, GB, vol. 21, No. 5, 1993, pp. 1155-1162.
Dyatkina, N., et al. "Modified Triphosphates of carbocyclic nucleoside analogues: synthesis, stability towards alkaline phosphatase and substrate properties for some DNA polymerases" Bioorganic and Medicinal Chemistry Letters, Oxford, GB, vol. 6, No. 22, Nov. 19, 1996, pp. 2639-2642.
Su, S-H., et al. "Novel non-nucleosidic phosphoramidites for oligonucleotide modification and labeling" Bioorganic and Medicinal Chemistry Letters, Oxford, GB, vol. 7, No. 13, Jul. 8, 1997, pp. 1639-1644.
Arzumanov Andrey, A., et al. "Gamma-Phosphate-substituted 2'-deoxynucleoside 5'-triphosphates as substrates for DNA polymerases" Journal of Biological Chemistry, vol. 271, No. 40, 1996, pp. 24389-24394.
Lundberg, K.S., et al. "High-fidelity amplification using a thermostable DNA polymerase isolated from *Pyrococcus furiosus*." Gene, 1991, vol. 108, No. 1, pp. 1-6.
Aslanidis, C., et al. "Ligation-independent cloning of PCR products (LIC-PCR)." Nucleic Acids Research, Sep. 20, 1990, vol. 18, No. 20, pp. 6069-6074.

* cited by examiner

*Primary Examiner*—Gary Benzion
*Assistant Examiner*—Heather G. Calamita
(74) *Attorney, Agent, or Firm*—Yonggang Ji

(57) ABSTRACT

A method of characterizing an analyte sample is provided that includes the steps of: (a) anchoring the analyte to a nucleic acid template of known sequence; (b) conducting a DNA polymerase reaction that includes the reaction of a template, a non-hydrolyzable primer, at least one terminal phosphate-labeled nucleotide, DNA polymerase, and an enzyme having 3'→5' exonuclease activity which reaction results in the production of labeled polyphosphate; (c) permitting the labeled polyphosphate to react with a phosphatase to produce a detectable species characteristic of the sample; (d) detecting the detectable species. The method may include the step of characterizing the nucleic acid sample based on the detection. Also provided are methods of analyzing multiple analytes in a sample, and kits for characterizing analyte samples.

34 Claims, 3 Drawing Sheets

SEQUENCE LISTING

<160> NUMBER OF SEQ ID NOS: 4

<210> SEQ ID NO 1
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 1
gttttcccag tcacgacgtt gta                                    23

<210> SEQ ID NO 2
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 2
gtcgttatac aacgtcgtga ctgggaaaac                             30

<210> SEQ ID NO 3
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 3
gtcgttctac aacgtcgtga ctgggaaaac                             30

<210> SEQ ID NO 4
<211> LENGTH: 57
<212> TYPE: DNA
<213> ORGANISM: artificial sequence
<220> FEATURE:
<223> OTHER INFORMATION: synthetic oligonucleotide

<400> SEQUENCE: 4
acgttttctt tattgtcagt cgacctagtc gctcgtttag agcgactagg        50
tcgactg                                                      57

ANALYTE DETECTION

CROSS REFERENCE TO RELATED APPLICATIONS

This application claims priority to U.S. provisional patent application Nos. 60/406,892, 60/406,893, and 60/406,894 all filed Aug. 29, 2002 and to U.S. patent application Ser. Nos. 10/230,576 filed Aug. 29, 2002 and 10/358,818 filed Feb. 5, 2003. This application is a continuation-in-part of U.S. patent application Ser. Nos. 10/113,030 now U.S. Pat. No. 7,052,839 and 10/113,025 now U.S. Pat. No. 7,033,762 both filed Apr. 1, 2002, all of which claim the benefit of U.S. provisional patent application No. 60/315,798 filed Aug. 29, 2001. The disclosures of these applications are incorporated herein by reference in their entireties.

FIELD OF INVENTION

The present invention relates generally to methods of detecting one or more analytes using terminal phosphate labeled nucleotides, including three or more phosphates as substrates for nucleic acid polymerases. The labels employed are enzyme-activatable and include chemiluminescent, fluorescent, electrochemical and chromophoric moieties as well as mass tags.

BACKGROUND OF INVENTION

Methods are known for detecting analytes in a sample with high specificity and sensitivity. These methods include antigen-antibody assays as well DNA hybridization based assays. Detection of analytes using immunodetection is well known in the art. Methods include direct labeling of antibodies using radioisotopes, fluorescent or chemiluminescent tags, or ELISA assays where an enzyme linked to the antibody catalyzes conversion of a chromogenic substrate to a detectable species. Latter are generally more desirable as multiple detectable moieties can be generated per binding event thereby increasing sensitivity. Similar methods have been incorporated into DNA hybridization based assays, which are generally more sensitive and in most diagnostic assays can be used at an earlier stage of disease progression. Enhanced sensitivity is achieved by first amplifying nucleic acid sequence based on the presence of a specific target sequence. Following amplification, the amplified sequences are detected and quantified. As a method of amplifying a nucleic acid sequence, the PCR (polymerase chain reaction) process is known. Presently, PCR is the most conventional means for in vitro amplification of nucleic acid. However, PCR has certain disadvantages, including the requirement for strict temperature control, inadequate quantification due to logarithmic amplification, and the danger of erroneous results brought about by simultaneous amplification of trace amounts of contaminated DNA. Additionally, except for nucleic acids, most other analytes are not easily amplified. In such cases, signal amplification methods are more desirable. These detect amplified decomposition products, i.e., a product or by-product of a reaction is amplified as the signal from a target analyte.

The traditional methods of amplifying the signal use enzyme linked to antibodies or polynucleotides and are limited by the amount of multiplexing one can achieve. There are only a few enzymes, such as alkaline phosphatase or horse radish peroxidase, that have been linked to antibodies or DNA probes. Other methods of signal amplification are based on nucleic acid metabolizing enzymes.

A cycling assay has been developed which utilizes λ-exonuclease to specifically cleave double stranded DNA (C. G. Copley et al., Bio Techniques, Vol. 13, No. 6, pp 882–892, 1992). This method involves hybridizing an oligonucleotide probe with a nucleic acid sequence complimentary thereto, allowing λ-exonuclease to act on the formed double-stranded DNA to decompose the hybridized probe. The probe is replaced by another probe, which is then decomposed. In this way, a cycling reaction repeats. In this method, the presence of a target DNA sequence is estimated by the detection of the decomposed probe. A disadvantage of this method is that the λ-exonuclease requires a probe which is phosphorylated at its 5'-terminal as the substrate. Following chemical synthesis of the probe by known methods, the 5'-terminal needs to be phosphorylated, and it is often difficult to confirm that all 5'-terminals are phosphorylated completely. An additional problem of this method is the low turnover number of cycling reactions, i.e., the number of times hybridization between the primer and target nucleotide occurs. The turnover number is low since the hybridization step must repeatedly occur.

An additional cycling assay by an exonuclease has been disclosed in EP 500224/A1. In this method, the synthesis of a DNA strand complimentary to a target DNA proceeds from a primer simultaneously with the decomposition of the same primer from the other side by a 5'→3' exonuclease such that another primer hybridizes with the target sequence in place of the decomposed primer hybridized before. Therefore, in a single cycle reaction both the synthesis of a complimentary strand by DNA polymerase as well as the degradation of the synthesized strand repeatedly occurs. A disadvantage of this method is the low turnover number, with the hybridization step being rate limiting in that it must repeatedly occur.

A further cycling assay for detection of a polynucleotide containing a specific sequence is disclosed in U.S. Pat. No. 5,849,487. This method relies on signal amplification and detection of decomposition products. This method includes using a combination of nucleic acid polymerase, 3'→5' exonuclease, a nuclease-resistant primer, a target nucleic acid, which may be DNA at limiting concentration, and at least one deoxynucleoside triphosphate (dNTP) to detect the target nucleic acid sequence. The method further includes synthesizing a complimentary strand being a nucleotide species located adjacent to the 3'-terminal of the nuclease-resistant primer, followed by decomposition of the nucleotide species joined to the end of the primer and detection of the resulting pyrophosphoric acid or deoxynucleoside monophosphate, the synthesis and decomposition of the nucleotide species being repeated one or more times. A disadvantage of this method as well as other detection methods presently widely in use is the need to separate labeled starting material from a final labeled product or by-product. Such separations generally require gel electrophoresis or immobilization of a target nucleic acid sequence onto a membrane for detection. For example, in U.S. Pat. No. 5,849,487, the deoxynucleoside monophosphate formed by a nuclease reaction is separated by chromotography and optically measured. Alternatively, the pyrophosphoric acid which is formed upon incorporation of a complimentary base by DNA polymerase may be allowed to react with adenosine-5'-phosphosulfate and adenosine triphosphate sulfurase to form adenosine triphosphate, which is then detected using a luciferin-luciferase reaction; this presents the disadvantage of requiring additional reagents and incubation steps.

It has been known that DNA and RNA polymerases are able to recognize and utilize nucleosides with a modification at or in place of the gamma position of the triphosphate moiety. It is further known that the ability of various polymerases to recognize and utilize gamma-modified nucleoside triphosphates appears to vary depending on the moiety attached to the gamma phosphate.

A colorimetric assay for monitoring RNA synthesis from RNA polymerases in the presence of a gamma-phosphate modified nucleotide has been reported (Ref. Vassiliou W, Epp J B, Wang B B, Del Vecchio A M, Widlanski T, Kao C C. Exploiting polymerase promiscuity: A simple colorimetric RNA polymerase assay. Virology. Sep. 1, 2000; 274(2): 429–37). In this report, RNA polymerase reactions were performed in the presence of a gamma-modified, alkaline phosphatase resistant nucleoside triphosphate which was modified at its gamma phosphate with a dinitrophenyl group. When RNA polymerase reactions were performed in the presence of this gamma-modified NTP as the sole nucleoside triphosphate and a homopolymeric template, it was found that RNA polymerase could recognize and utilize the modified NTP. Moreover, when the polymerase reactions were performed in the presence of an alkaline phosphatase, which digested the p-nitrophenyl pyrophosphate aldo-product of a phosphoryl transfer to the chromogenic p-nitrophenylate, an increase in absorbance was reported. A disadvantage of this detection method is that the real-time colorimetric assay, performed in the presence of an alkaline phosphatase, only works with a homopolymeric template.

It would, therefore, be of benefit to provide methods of detecting and characterizing an analyte, which methods would include utilization of terminal-phosphate-labeled nucleotides as substrates for DNA polymerase in a cycling assay by an exonuclease. It would further be of benefit if such methods would employ enzyme-activatable labels at the terminal phosphate of the nucleotide for production of an amplified detectable species from a target nucleic acid which would eliminate the need to separate labeled starting materials from labeled products or by-products. Moreover, it would be highly desirable if such methods for detecting and characterizing nucleic acids would allow for real-time monitoring of a heteropolymeric target nucleic acid using routine lab instrumentation. Finally, it is additionally desirable if such methods are easily multiplexed to analyze four or more analytes per reaction compartment simultaneously or in sequential manner.

SUMMARY OF INVENTION

An aspect of the present invention is to provide a method of detecting an analyte in which a 3'→5' DNA exonuclease acting on DNA, is used together with DNA polymerase, a phosphatase and a primer-template combination with an anchoring moiety useful for anchoring the primer, the template or primer-template complex to the analyte so that a signal from the target analyte can be amplified and detected without the need for further operations such as separation of labeled reaction products from labeled starting materials.

The present invention provides methods for detecting an analyte. One method includes the steps of: (a) anchoring a nucleic acid template with an anchoring moiety to the target analyte, (b) conducting a DNA polymerase reaction, the reaction including the reaction of the template, a non-hydrolyzable primer, at least one terminal phosphate-labeled nucleotide, DNA polymerase and an enzyme having 3'→5' exonuclease activity, wherein the enzyme may be selected from DNA polymerases, exonucleases, and combinations thereof, which reaction results in the production of labeled polyphosphate; (c) permitting the labeled polyphosphate to react with a phosphatase to produce a detectable species; and (d) detecting the detectable species.

Another aspect of the invention relates to a method of detecting multiple analytes in a sample including the steps of: a) anchoring to each analyte a specific template nucleic acid with a unique base at the site opposite from the complementary nucleotide being added (b) conducting a DNA polymerase reaction, the reaction including the reaction of the template, a non-hydrolyzable primer, two or more terminal phosphate-labeled nucleotides with different labels, DNA polymerase and an enzyme having 3'→5' exonuclease activity, wherein the enzyme may be selected from DNA polymerases, exonucleases, and combinations thereof, which reaction results in the production of labeled polyphosphate; (c) permitting the labeled polyphosphate to react with a phosphatase to produce a detectable species; and (d) detecting the detectable species. With this method it is possible to detect four analytes simultaneously using the natural bases. Further multiplexing can be achieved by using unnatural bases that have their own complementary partners and are not readily misincorporated opposite other natural or unnatural bases. Examples of these unnatural bases are cited in Lei Wang et. al. J. Am. Chem. Soc. 2000, 122, 5010–5011 and references therein and are incorporated herein by reference.

Another aspect of the current invention relates to an alternative way to analyze multiple analytes in a reaction compartment is to (a) attach a specific template nucleic acid sequence to each analyte (b) anchor the analytes to the reaction compartment surface; (c) conduct a DNA polymerase reaction, the reaction comprising the reaction of a particular template sequence on an analyte, a complementary non-hydrolyzable primer, at least one terminal phosphate-labeled nucleotide, DNA polymerase and an enzyme having 3'→5' exonuclease activity, wherein the enzyme may be selected from DNA polymerases, exonucleases, and combinations thereof, which reaction results in the production of labeled polyphosphate; (d) permitting the labeled polyphosphate to react with a phosphatase to produce a detectable species; and (e) detecting the detectable species; (f) washing all the unanchored components and (g) repeating the process with a different non-hydrolyzable primer complementary to a target sequence of a different analyte.

Further provided is a method of detecting an analyte including the steps of: (a) anchoring a nucleic acid template to the target analyte, (b) conducting a DNA polymerase reaction, the reaction comprising the reaction of the template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; and (c) detecting the labeled polyphosphate.

Another aspect of the invention relates to a method of detecting multiple analytes in a sample including the steps of: (a) anchoring to the target analyte a nucleic acid template with a unique base at the site opposite from the complementary nucleotide being added, (b) conducting a DNA polymerase reaction, the reaction comprising the reaction of the template, a non-hydrolyzable primer, two or more terminal phosphate-labeled nucleotides having 4 or more phosphate groups in the polyphosphate chain and each bearing a different label, DNA polymerase and an enzyme having 3'→5' exonuclease activity, wherein the enzyme may be selected from DNA polymerases, exonucleases and combinations thereof, which reaction results in the production of labeled polyphosphate; (c) detecting the labeled polyphosphate.

Another aspect of the current invention relates to detecting multiple analytes in a reaction compartment is to (a) anchor a unique nucleic acid template to, each target analyte, (b) anchor the analytes to the reaction compartment surface; (c) conduct a DNA polymerase reaction, the reaction comprising the reaction of a particular template sequence on an analyte, a complementary non-hydrolyzable primer, at least one terminal phosphate-labeled nucleotides having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (d) detecting the labeled polyphosphate; (e) washing all the unanchored components and (f) repeating the process with a different non-hydrolyzable primer complementary to a target sequence of a different analyte.

Another aspect of the invention relates to a method of detecting an analyte including the steps of: (a) anchoring a nucleic acid template to the target analyte, (b) conducting a DNA polymerase reaction, the reaction comprising the reaction of the template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (c) permitting the labeled polyphosphate to react with a phosphatase to produce a detectable species; and (d) detecting the detectable species.

Another aspect of the invention relates to a method of detecting multiple analytes in a sample including the steps of: (a) anchoring a unique nucleic acid template to each target analyte, (b) conducting a DNA polymerase reaction, the reaction comprising the reaction of a particular template nucleic acid sequence on an analyte, a non-hydrolyzable primer, two or more terminal phosphate-labeled nucleotides having 4 or more phosphate groups in the polyphosphate chain and each bearing a different label, DNA polymerase and an enzyme having 3'→5' exonuclease activity, wherein the enzyme may be selected from DNA polymerases, exonucleases and combinations thereof, which reaction results in the production of labeled polyphosphate; (c) permitting the labeled polyphosphate to react with a phosphatase to produce a detectable species; and (d) detecting the detectable species.

Another aspect of current invention relates to detection of multiple analytes in a reaction compartment is to (a) anchor a unique nucleic acid template to each target analyte, (b) anchor the analytes to the reaction compartment surface; (c) conduct a DNA polymerase reaction, the reaction comprising the reaction of a particular template sequence on an analyte, a complementary non-hydrolyzable primer, at least one terminal phosphate-labeled nucleotides having 4 or more phosphate groups in the polyphosphate chain, a DNA polymerase and an enzyme having 3'→5' exonuclease activity, wherein the enzyme may be selected from DNA polymerases, exonucleases and combinations thereof, which reaction results in the production of labeled polyphosphate; (d) permitting the labeled polyphosphate to react with a phosphatase to produce a detectable species; (e) detecting the detectable species; (f) washing all the unanchored components and repeating the process with a different non-hydrolyzable primer complementary to a target sequence of a different analyte.

The invention further provides methods of characterizing an analyte. For example, the invention provides a method including the steps of: (a) anchoring a nucleic acid template to the target analyte, (b) conducting a DNA polymerase reaction, the reaction including the reaction of the template, a non-hydrolyzable primer, at least one terminal phosphate-labeled nucleotide, DNA polymerase and an enzyme having 3'→5' exonuclease activity, wherein the enzyme may be a DNA polymerase, exonuclease or a combination thereof, which reaction results in the production of labeled polyphosphate; (b) permitting the labeled polyphosphate to react with a phosphatase to produce a detectable species; (c) detecting the detectable species; and (d) characterizing the analyte based on the detection.

Further encompassed by the invention is a method of characterizing an analyte including the steps of: (a) anchoring a nucleic acid template to the target analyte, (b) conducting a DNA polymerase reaction, the reaction comprising the reaction of the template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (c) detecting said labeled polyphosphate; and (d) characterizing the analyte based on the detection.

Also provided is a method of detecting an analyte including the steps of: (a) anchoring a nucleic acid template to the target analyte, (b) conducting a DNA polymerase reaction, the reaction comprising the reaction of the template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (c) permitting the labeled polyphosphate to react with an alkaline phosphatase to produce a detectable species having a signal profile characteristic of the analyte; (d) detecting the detectable species; and (e) characterizing the analyte based on the signal profile.

Similar methods as described above can be used for characterization of multiple analytes in a reaction compartment. In the specifications listed above it is equally feasible to attach the non-hydrolyzable primer to the analyte and provide the template in solution. In some preferred embodiments of the above specifications, the non-hydrolyzable primer and template are joined together in a hair-pin structure shown in FIG. 1 and the analyte binding functionality is on the loop of the hairpin oligonucleotide. In most preferred embodiments of above specifications, before conducting the DNA polymerase reaction, unanchored nucleic acid template is removed from the anchored material. Depending on the target analyte this can be achieved by a number of methods including simple washing, precipitation, filteration, or by chromatographic or electrophoretic methods.

Further encompassed by the invention are kits for detecting an analyte, one kit including: (a) at least one terminal-phosphate-labeled nucleotide; (b) a DNA polymerase; (c) a phosphatase, (d) a template and a complementary non-hydrolyzable primer, one of which bears an anchoring moiety; and (e) a nuclease with enzymatic activity sufficient to decompose DNA in the 3'→5' direction.

A further kit for detection of an analyte is provided which includes: (a) at least one terminal-phosphate-labeled nucleotide; (b) a phosphatase, (c) a template and a complementary non-hydrolyzable primer, one of which bears an anchoring moiety; and (d) a DNA polymerase with enzymatic activity sufficient to decompose DNA in the 3'→5' direction.

A further aspect of the present invention is to provide a kit for the detection of an analyte, one kit including: (a) at least one terminal-phosphate-labeled nucleotide; (b) a DNA polymerase; (c) a phosphatase; (d) a hairpin template-primer combination with an anchoring moiety and a non-hydrolyzable 3'-end; and (e) a nuclease with enzymatic activity sufficient to decompose DNA in the 3'→5' direction.

Lastly, a kit is provided herein for the detection of an analyte which includes: (a) at least one terminal-phosphate-labeled nucleotide; (b) a phosphatase (c) a hairpin template-primer combination with an anchoring moiety and a non-hydrolyzable 3'-end; and (d) a DNA polymerase with enzymatic activity sufficient to decompose DNA in a 3'→5' direction.

DESCRIPTION OF INVENTION

Figure 1:
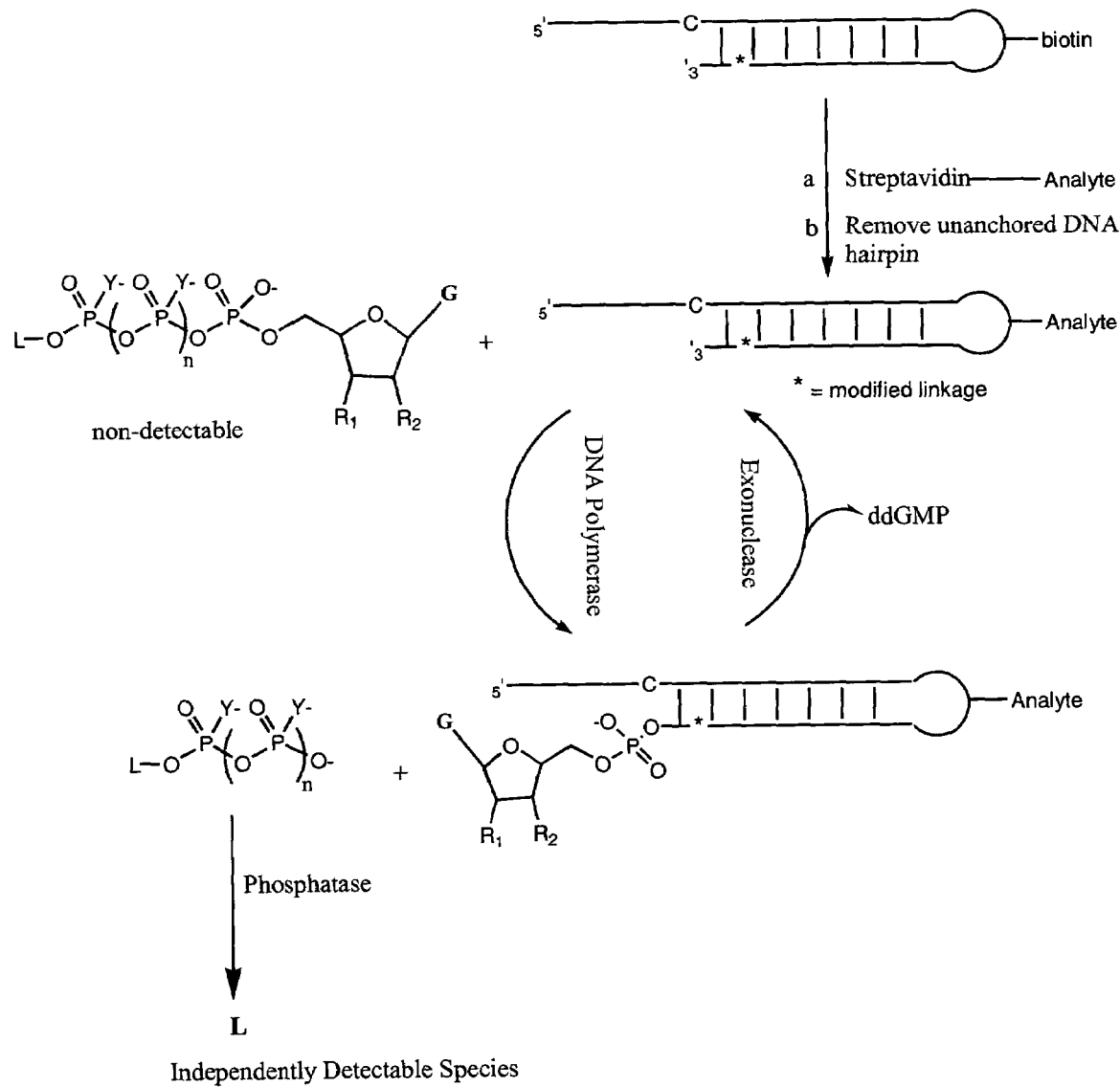
FIG. 1 shows an embodiment of a method of the present invention where a hairpin looped DNA primer-template with non-hydrolyzable 3'-end is attached to the target analyte and a terminal-phosphate-labeled nucleotide complimentary in sequence to template is joined to the 3' end of a nuclease-resistant primer, followed by decomposition thereof to effect a cycling assay in which the labeled polyphosphate by-product of nucleotide incorporation reacts with an alkaline phosphatase to produce a detectable species.

The term analyte as defined herein includes, but is not limited to, a biomolecule, a whole cell or a commercially important substrate that may need to be tracked for its distribution or identification. Biomolecules include nucleic acids, peptides, proteins, oligosaccharides, lipids, antigens, etc., while commercially important substrates include, but are not limited to, organic and inorganic polymers or products made therefrom.

The term "phosphatase" as defined herein includes alkaline and acid phosphatases, 5'-nucleotidases, and phosphate or polyphosphate transferring enzymes which can not cleave a terminal phosphate labeled nucleoside polyphosphate, but after incorporation of the nucleoside monophosphate by a polymerase, can remove the phosphate units from the resultant dye polyphosphate.

The term "nucleoside" as defined herein is a compound including a purine deazapurine, or pyrimidine base linked to a sugar or a sugar substitute, such as a carbocyclic or acyclic linker at the 1' position or equivalent position and includes 2'-deoxy and 2'-hydroxyl, 2',3'-dideoxy forms, as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid sequence to which the primer is targeted.

The term "anchoring" means attaching through covalent or non-covalent interactions.

The present invention relates to methods of detecting and characterizing one or more analytes in a sample wherein the analyte is marked by the attachment of a nucleic acid template or a non-hydrolyzable primer or a combination thereof in the form of a DNA hairpin and a convenient assay is used for monitoring the addition of a terminal-phosphate-labeled nucleotide which is complimentary to a specific base in the target nucleic acid, onto the 3'-terminal of a non-hydrolyzable primer followed by nuclease decomposition thereof. DNA polymerases synthesize oligonucleotides via transfer of a nucleoside monophosphate from a deoxynucleoside triphosphate (dNTP) to the 3' hydroxyl of a growing oligonucleotide chain.

The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions.

The methods provided by this invention utilize a nucleoside polyphosphate analogue, such as a deoxynucleoside polyphosphate or dideoxynucleoside polyphosphate analogue with an electrochemical label, mass tag, or a chromogenic, chemiluminescent, or fluorescent dye label attached to the terminal-phosphate. When a nucleic acid polymerase uses this analogue as a substrate, an enzyme-activatable label is present on the inorganic polyphosphate by-product of phosphoryl transfer. Cleavage of the polyphosphate product of phosphoryl transfer by a phosphatase, results in a detectable change in the label attached thereon. For example, if 3-cyanoumbelliferone dye is attached via its hydroxyl group to the terminal phosphate position of a nucleotide, the dye is not fluorescent when excited at 408 nm and it is not a substrate for alkaline phosphatase. Once this nucleotide is incorporated into DNA, the released dye inorganic polyphosphate (which also is not fluorescent when excited at 408 nm) is a substrate for alkaline phosphatase. Once de-phosphorylated, the dye becomes fluorescent when excited at 408 nm and hence detectable. The specific analysis of the polyphosphate product can be carried out in the same reaction solution as, the polymerase and exonuclease reactions, with no need to separate reaction products from starting materials. This allows for the detection and, optionally, quantification of nucleic acids formed during polymerase reactions and hence an analyte if the nucleic acid is attached to the analyte using routine instrumentation such as fluorimeters or spectrophotometers.

It is noted that while RNA and DNA polymerases are able to recognize nucleotides with modified terminal phosphoryl groups, the inventors have determined that this starting material is not a substrate for phosphatases. The scheme below shows relevant molecules in the method of this invention; namely the terminal-phosphate-labeled nucleotide, the labeled polyphosphate by-product and the enzyme-activated label.

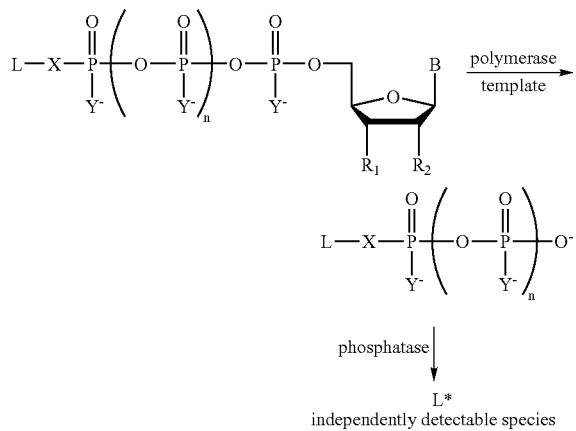

In the scheme above, n is 1 or greater, R1 and R2 are independently H, SH, SR, F, Br, Cl, I, N3, NH2, NHR, OR or OH; B is a natural or modified nucleoside base; X is O, S, or NH; Y is O, S, or BH3 and L is a phosphatase activatable label which may be a chromogenic, fluorogenic, or chemiluminescent molecule, mass tag or electrochemically detectable moiety. A mass tag is a small molecular weight moiety suitable for mass spectrometry that is readily distinguishable from other reaction products due to difference in mass. An electrochemical tag is an easily oxidizable or reducible species. It has been discovered that when n is 2 or greater, the nucleotides are significantly better substrates for polymerases than when n is 1. Therefore, in preferred embodiments of the present invention, n is 2, 3 or 4. In further desired embodiments of the present invention, X and Y are O; and R1 and R2 are independently H or OH; B is a nucleoside base and L is a label which may be a chromogenic, fluorogenic or a chemiluminescent molecule.

In one embodiment of the method of detecting an analyte provided herein, the steps include anchoring a nucleic acid template to the analyte, conducting a DNA polymerase reaction, the reaction including the reaction of the template, a non-hydrolyzable primer, at least one terminal phosphate-labeled nucleotide, DNA polymerase and an enzyme having 3'→5' exonuclease activity, wherein the enzyme may be selected from DNA polymerases, exonucleases and combinations thereof, which reaction results in the production of labeled polyphosphate provided the terminal phosphate-labeled nucleotide is complementary to the template; permitting the labeled polyphosphate to react with a phosphatase, such as alkaline phosphatase, to produce a detectable species; and detecting the detectable species.

In the methods of characterizing analyte sample provided by this invention, the target analyte may be characterized by determining the presence or absence of the detectable species. Moreover, the detectable species may have a characteristic staining profile or signal profile associated with it, the profile being characteristic of the sample. This allows for characterization of the analyte target based on the unique profile of the detectable species.

FIG. 1 shows the general scheme employed for each of the methods described above. In this scheme, n is 1 or greater, R1 and R2 are independently H, OH, SH, SR, F, Cl, Br, I, N3, NH2 or OR; G is guanine, or representative of a natural or modified nucleoside base; C is cytosine or representative of the base complimentary to the added nucleotide; Y is O, S, or BH3 and L is a chromogenic, fluorogenic, chemiluminescent, or electrochemical label or mass tag which preferably becomes independently detectable when the phosphate is removed. As shown in FIG. 1, a DNA hairpin with non-hydrolyzable, but extendable 3'-end is attached to an analyte. After separation of the unbound DNA hairpin, the DNA polymerase reaction is conducted in the presence of the hairpin anchored analyte and at least one terminal-phosphate-labeled nucleotide under conditions to cause a nucleoside monophosphate derived from the terminal-phosphate-labeled nucleotide to join to the 3'-terminal end of the nuclease-resistant DNA hairpin. This is accompanied by the concomitant formation of a labeled product which may not be independently detectable. The labeled polyphosphate concomitantly formed during incorporation of the nucleotide species is permitted to react with a phosphatase to produce an independently detectable species which serves as the signal from the target polynucleotide. Addition of a complimentary nucleotide species to the 3'-terminal of the primer is followed by decomposition thereof by the reaction of a 3'→5' exonuclease which may be associated with the DNA polymerase itself. The synthesis and decomposition of the complementary strand being essentially the nucleotide species, is repeated one or more times to effect a cycling assay.

In the methods described above, the polymerase reaction may be conducted in the presence of a phosphatase, such as alkaline phosphatase or a phosphate transferring enzyme, which converts the labeled polyphosphate product to the detectable label. As such, convenient assays are established for detecting and characterizing an analyte that allows for continuous, real-time monitoring of detectable species formation. This represents a homogeneous assay format in that it can be performed in a single tube using analytes pre-anchored with DNA template, primer or combined template primer hairpin.

It is noted that in embodiments including terminal phosphate-labeled nucleotides having four or more phosphates in the polyphosphate chain, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal phosphate labeled nucleotide, the label may be partially quenched by the base. Upon incorporation of the nucleoside monophosphate, the labeled polyphosphate by-product may be detected due to its enhanced fluorescence. Alternatively, it is possible to physically separate the labeled polyphosphate product by chromatographic separation methods before identification by fluorescence, color, chemiluminescence, or electrochemical detection. In addition, mass spectrometry could be used to detect the products by mass difference.

The detectable species may be produced in amounts substantially proportional to the amount of target analyte and, as such, is a signal for the amount of the target analyte. The methods herein described may further include the step of quantifying the target analyte based on the amount of detectable species produced during the reaction. The step of quantifying the target analyte is desired to be done by comparison of spectra produced by the detectable species with known target quantities.

In the present invention, once hybridized, the oligonucleotide primer can repeatedly function so as to permit the reaction to proceed quantitatively in an at least equal molar amount relative to the template nucleotide sequence. When used separately the ratio of the oligonucleotide template to primer useful in the methods of the present invention should be that sufficient to attain a favorable hybridization. In general, a sensitive assay can be attained by the presence of a template primer ratio of one and desirably in a 5-fold excess of one over the other.

The methods provided by the present invention may further include the step of including one or more additional detection agents in the DNA polymerase reaction. The additional detection agent may be capable of a response which is detectably different from the detectable species. For example, the additional detection agent may be an antibody.

The target analyte of the present invention includes, but is not limited to, biomolecules such as nucleic acids, peptides, proteins, antigens, lipids, complex sugars; whole cells and synthetic polymers and/or substrates.

The terminal-phosphate-labeled nucleotide useful in the methods and kits of the present invention may be represented by Formula I:

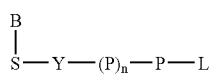

wherein P=phosphate (PO₃) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

For purposes of the methods of the present invention, useful carbocyclic moieties have been described by Ferraro, M. and Gotor, V. in Chem Rev. 2000, volume 100, 4319–48. Suitable sugar moieties are described by Joeng, L. S. et al., in J Med. Chem. 1993, vol. 356, 2627–38; by Kim H. O. et al., in J Med. Chem. 193, vol. 36, 30–7; and by Eschenmosser A., in Science 1999, vol. 284, 2118–2124. Moreover, useful acyclic moieties have been described by Martinez, C. I., et al., in Nucleic Acids Research 1999, vol. 27, 1271–1274; by Martinez, C. I., et al., in Bioorganic & Medicinal Chemistry Letters 1997, vol. 7, 3013–3016; and in U.S. Pat. No. 5,558,991 to Trainor, G. L. Structures for these moieties are shown below, where for all moieties R may be H, OH, NHR, lower alkyl and aryl; for the sugar moieties X and Y are independently O, S, or NH; and for the acyclic moieties, X=O, S, NH, NR.

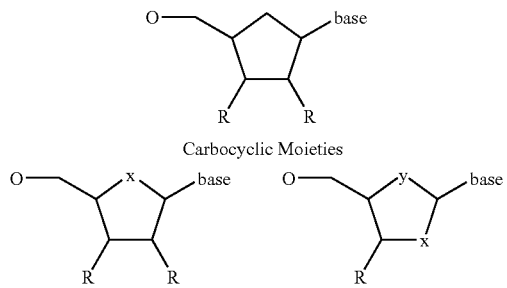

Carbocyclic Moieties

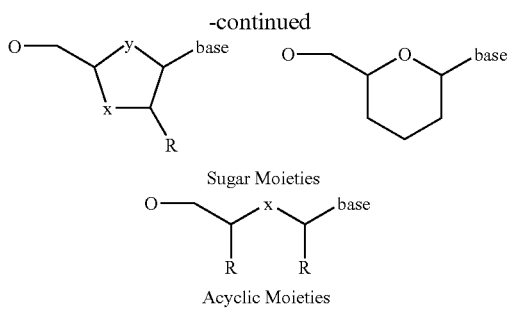

Sugar Moieties

Acyclic Moieties

In certain embodiments, the sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'mercaptoriboxyl, 2'-alkylthioribosyl, carbocyclic, acyclic and other modified sugars.

Moreover, in Formula I above, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The enzyme-activatable label attached at the terminal phosphate position of the nucleotide may be selected from 1,2-dioxetane chemiluminescent compounds, fluorogenic dyes, chromogenic dyes, mass tags, electrochemical tags or combinations thereof. This would allow the detectable species to be detectable by the presence of any one of color, fluorescence emission, chemiluminescence, or a combination thereof.

The enzyme-activatable label may also be a chemical moiety that becomes a substrate for an additional chemical or enzymatic reaction that results in the production of a detectable signal.

Wherein the phosphorylated label shown in Formula I above is a fluorogenic moiety, it is desirably selected from one of the following examples (shown as their phosphate esters): 2-(5'-chloro-2'-phosphoryloxyphenyl)-6-chloro-4-(3H)-quinazolinone, sold under the trade name ELF 97 (Molecular Probes, Inc.), fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacridin-2-one-7-yl phosphate, and 6,8-difluoro-4-methylumbelliferyl phosphate. Structures of these dyes are shown below:

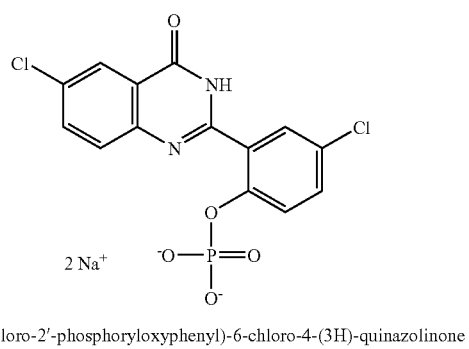

2-(5'-chloro-2'-phosphoryloxyphenyl)-6-chloro-4-(3H)-quinazolinone

-continued

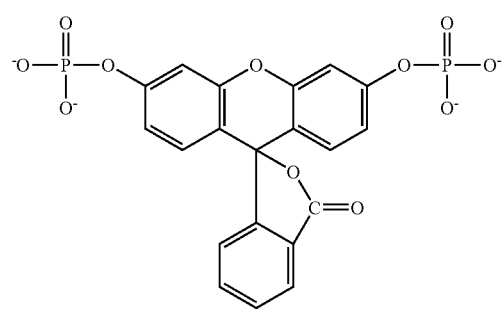

fluorescein diphosphate

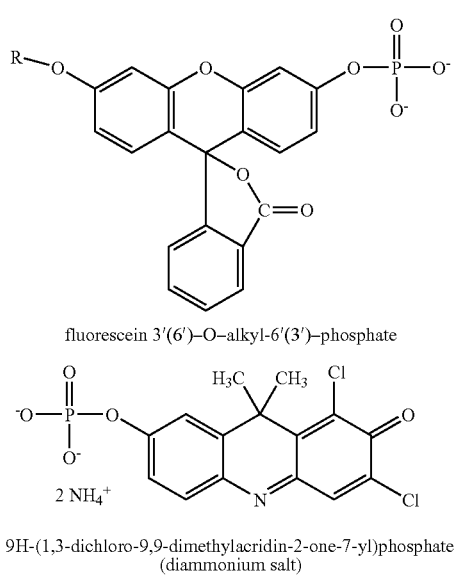

fluorescein 3'(6')–O–alkyl-6'(3')–phosphate

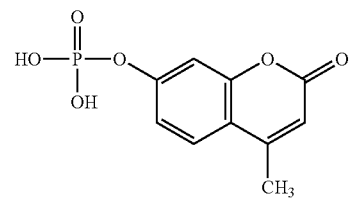

9H-(1,3-dichloro-9,9-dimethylacridin-2-one-7-yl)phosphate
(diammonium salt)

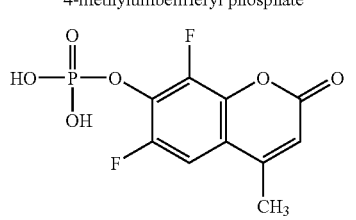

4-methylumbelliferyl phosphate

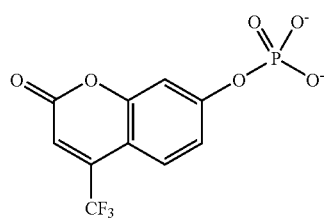

6,8-difluoro-4-methylumbelliferyl phosphate

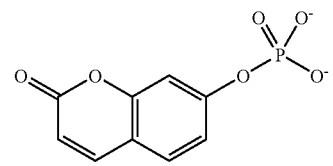

4-Trifluoromethylumbelliferyl phosphate

-continued

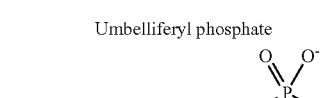

Umbelliferyl phosphate

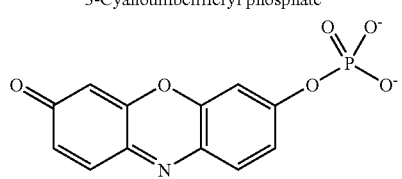

3-Cyanoumbelliferyl phosphate

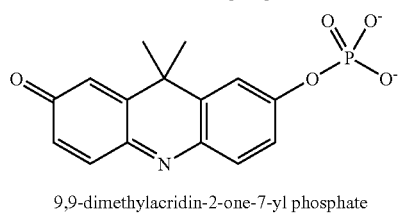

Resorufin phosphate

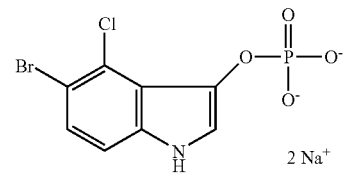

9,9-dimethylacridin-2-one-7-yl phosphate

Wherein the phosphorylated label shown in Formula I above is a chromogenic moiety, it may be selected from the following moieties (shown as the phosphate esters): 5-bromo-4-chloro-3-indolyl phosphate, 3-indolyl phosphate, p-nitrophenyl phosphate and derivatives thereof. The structures of these chromogenic dyes are shown below:

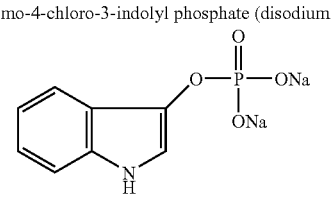

5-bromo-4-chloro-3-indolyl phosphate (disodium salt)

3-indolyl phosphate (disodium salt)

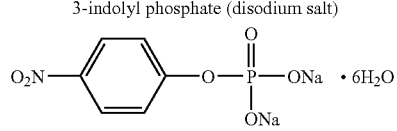

p-nitrophenyl phosphate

The moiety at the terminal phosphate position may further be a chemiluminescent compound wherein it is desired that it is an alkaline phosphatase-activated 1,2-dioxetane compound. The phosphate esters of the 1,2-dioxetane compound may include, but are not limited to, disodium 2-chloro-5-(4-methoxyspiro[1,2-dioxetane-3,2'-(5-chloro-)tricyclo[3,3,1-1$^{3,7}$]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3"-phosphoryloxy) phenyl-1,2-dioxetane, sold under the trade name AMPPD (Tropix). The structures of these commercially available dioxetane compounds are disclosed in U.S. Pat. Nos. 5,582,980, 5,112,960 and 4,978,614, respectively, and are shown below:

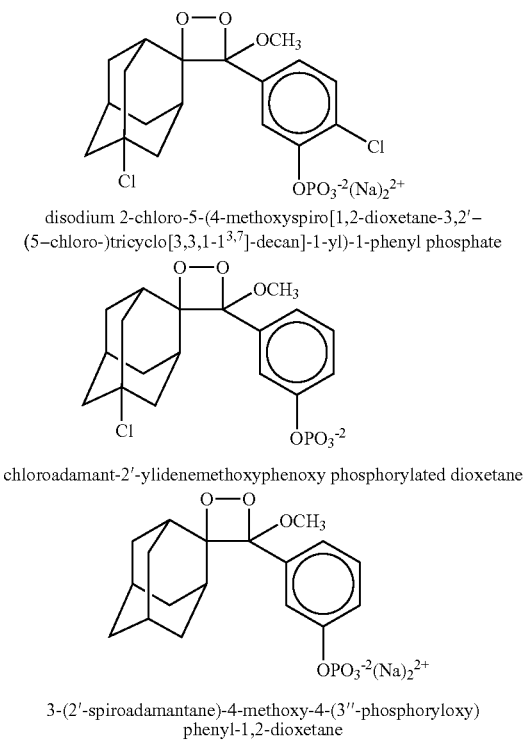

disodium 2-chloro-5-(4-methoxyspiro[1,2-dioxetane-3,2'–(5–chloro-)tricyclo[3,3,1-1$^{3,7}$]-decan]-1-yl)-1-phenyl phosphate chloroadamant-2'-ylidenemethoxyphenoxy phosphorylated dioxetane 3-(2'-spiroadamantane)-4-methoxy-4-(3"-phosphoryloxy) phenyl-1,2-dioxetane In the methods of the present invention, the non-hydrolyzable primer should be nuclease-resistant in order to prevent its decomposition by the 3'→5' exonuclease present in the system.

As described above, the 3'→5' exonuclease activity may be associated with the DNA polymerase itself. Suitable DNA polymerases for use in the present invention include, but are not limited to, the Klenow fragment of DNA polymerase I, Phi 29 DNA polymerase, DNA polymerase I, T4 DNA polymerase Thermo Sequenase (Amersham Biosciences Corporation), Amplitaq FS (Applied Biosystems), reverse transcriptase, and T7 DNA polymerase.

Methods for synthesizing nuclease-resistant oligonucleotide primers are not particularly limited, and any suitable method known in the art may be used. For example, in one embodiment of the method provided by the invention, the non-hydrolyzable primer is phosphorothioated at the 3'-most phosphodiester linkage terminal. Methods of chemically synthesizing an oligonucleotide primer having nuclease resistance by introducing a phosphorothioate bond into the target site of the primer are well known. In one method, the primer may be chemically synthesized using a modified phosphoramidite method in which the usual oxidation step by iodine water is replaced with an oxidation treatment with a reagent suitable for phosphorothioation, such that a phosphorothioate bond may be introduced in place of the usual phosphodiester bond. One suitable reagent for phosphorothioation is Beaucage's Reagent (3H-1,2-benzodithiole-3-one 1,1-dioxide). This method can be used to introduce a phosphorothioate bond into the primer at any chosen site, including at the 3'-most phosphodiester linkage.

An alternative means of preparing an oligonucleotide primer with a phosphorothioate bond prior to the time of analysis, is via DNA polymerase incorporation of a nucleotide analog in which an oxygen atom at the α-position is replaced by sulfur. Such substituted compounds are referred to as α-S-deoxynucleoside triphosphates. A DNA polymerase can incorporate the sulfur-substituted analog in place of deoxynucleoside triphosphate to give a phosphorothioated oligonucleotide primer containing nuclease resistance.

In any event, the presence of a phosphorothioate bond in place of a phosphodiester bond in the vicinity of the 3'-terminal of the oligonucleotide primer confers a resistance on the part of the primer to an exonuclease cleaving from the 3'-terminal side. The oligonucleotide primer is sufficiently non-hydrolyzable by the introduction of only a single phosphorothioate bond.

Methods for anchoring oligonucleotides to other substrates are well known in the art and include non-covalent binding such as biotin-streptavidin binding and covalent binding achieved by reacting functionalized oligonucleotides, e.g., amine functionalized oligonucleotides with activated acids, aldehydes, epoxides, etc., or thiol modified nucleotides with activated haloacetamide or vice versa.

Reaction conditions such as buffer, pH, and temperature should be selected to achieve sufficient hybridization, polymerase, nuclease, and phosphatase activities. Temperatures suitable for hybridization depend on the homology between the oligonucleotide primer and the target sequence, but are expected to be in the range of about 20° to about 60° C. The pH values are desired to be in the range of about 7 to 9 in a suitable buffer such as Tris-HCl buffer or HEPES.

The present invention is characterized in that following the anchoring step of a nucleic acid template or primer or a combination of two as described above to the analyte, at least one terminal-phosphate-labeled deoxynucleoside polyphosphate, a complementary oligonucleotide if not already present on the anchored analyte, a DNA polymerase, a nuclease (which may be associated with the polymerase), and a phosphatase are added to the system so that a nucleotide located next to the 3'-terminal of the primer and complimentary to the target nucleic acid is incorporated, followed by decomposition thereof and detection of a detectable species which acts as the signal from the target analyte, the synthesis and decomposition of the complimentary strand being repeated one or more times to effect a cycling assay for amplification of the signal.

It is well within the contemplation of the present invention that the amplification reaction could be performed using a polymerase and a single stranded nuclease (which could be an intrinsic property of the polymerase or a separate enzyme). The reaction is thermally cycled, allowing the extension of the primer by polymerase during low temperature, and removal of the added base by nuclease during high temperature. This would allow the user to control the amount of amplification, as it would be dependant on the number of thermal cycles which were performed.

EXAMPLES

The following examples illustrate certain preferred embodiments of the illustration that are not intended to be illustrative of all embodiments.

Example 1

Preparation of γ(7-Hydroxy-3H-Phenoxazin-3-one) ddGTP (γ-Resorufin-ddGTP)

ddGTP (125 µl of 86.7 mM solution, 10.8 µmol) was coevaporated with anhydrous DMF (3×0.25 ml). To this, DCC (5 eq.) was added and the mixture was again coevaporated with anhydrous DMF (0.25 ml). Residue was taken in anhydrous DMF (1 ml) and the reaction was stirred at room temperature over a weekend. Resorufin (20 eq.) was coevaporated with anhydrous DMF (2×1 ml) and ddGTP trimetaphosphate from the above cyclization step was added, followed by 20 eq. of triethylamine. After 2 weeks, the reaction mixture was concentrated on a rotary evaporator and the residue was extracted with water (3×2 ml) and filtered. The filtrate was purified on an Xterra RP C18 (19×100 mm) column using 0–30% acetonitrile in 0.1 M triethylammonium bicarbonate (pH 6.7) in 5 column volumes and 30–50% acetonitrile in 1 column volume. The pure fraction was concentrated on a rotavap and coevaporated with methanol (2×5 ml). The residue was dissolved in water (1.5 ml) to give a 0.5 mM solution. HPLC purity at 260 nm>98%, at 470 nm>97.5%. UV/VIS=251 and 472 nm. MS: M−1=685.10 (calc. 685.03).

DMF (0.5 ml) and reaction was stirred at room temperature. After overnight 7-hydroxy-3-cyanocoumarin (33.3 mg, 20 eq.) and TEA (25 µl, 20 eq.), were added and mixture was stirred at RT. After 1 day, HPLC analysis indicated a major product (55% at 254 nm) at 8.1 min with another minor product at 10 min (~10%). No significant change occurred after another day. Reaction mixture was concentrated on rotary evaporator and residue was extracted with 3×2 ml water and filtered. Aq solution was concentrated and purified on C18 using 0–30% acetonitrile in 0.1 M TEAB (pH 6.7) in 30 min and 30–50% acetonitrile in 10 min, flow rate 15 ml/min. Main peak was collected in 3 fractions. HPLC of the main peak (fr. 2) showed a purity of 95.6% at 254 nm and 98.1% at 335 nm. It was concentrated on rotary evaporator (at RT), coevaporated with MeOH (2×) and water (1×). Residue was dissolved in 0.5 ml water. A 5 µl sample was diluted to 1 ml for UV analysis. A346 nm=0.784. Assuming an extinction coeff. of 20,000 (reported for 7-ethoxy-3-cyanocoumarin, Molecular Probes Catalog), concentration=7.84 mM. Yield=3.92 µmol, 44%. Sample was repurified on C18 column using same method as above. Sample peak was collected in 3 fractions. Fractions 2 & 3, with >98% purity at 254 nm and >99.5% purity at 340 nm, were combined. After concentration, residue was coevaporated with MeOH (2×) and water (1×). Sample was dissolved in water (1 ml) to give a 2.77 mM solution. MS: M−=642.98 au (calc 643.00 au), UV $\lambda_A$=263 & 346 nm. The cyanocoumarin dye attached to the gamma phosphate of ddATP is

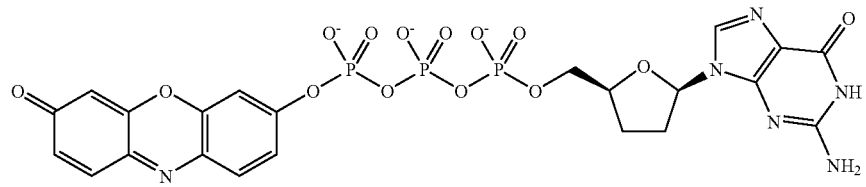

(7-Hydroxy-3H-Phenoxazin-3-one)ddGTP(γ-Resorufin-ddGTP)

Example 2

Preparation of γ-(3-Cyanocoumarinyl)ddATP (γCNCoumarin-ddATP)

ddATP (100 µl of 89 mM solution, >96%) was coevaporated with anhydrous DMF (2×1 ml). To this DCC (9.2 mg, 5 eq.) was added and mixture was again coevaporated with anhydrous DMF (1 ml). Residue was taken in anhydrous fluorescent with an excitation maximum of 346 nm and an emission maximum of about 411 nm. Upon hydrolysis of the phosphate ester to release the free coumarin dye, the spectrum changes with excitation maximum of about 408 nm and emission maximum of about 450 nm. This change is readily detected by simple fluorescence measurements or color change. Synthesis of gamma nucleotides has been generally described by Arzumanov, A, et al in J Biol Chem. (1996) October 4;271(40):24389–94.

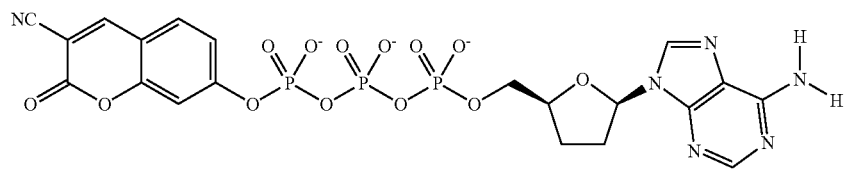

γ–(3-cyanocoumarinyl)dideoxyadenosine-5′-triphosphate
(γCNCoumarin-ddATP)

Example 3

Preparation of δ-9H(1,3-dichloro-9,9-dimethylacridin-2-one-7-yl)-dideoxythymidine-5'-tetraphosphate (ddT4P-DDAO)

ddTTP (100 μl of 80 mM solution) was coevaporated with anhydrous dimethylformamide (DMF, 2×1 ml). To this dicyclohexylcarbodimide (8.3 mg. 5 eq.) was added and the mixture was again coevaporated with anhydrous DMF (1 ml). Residue was taken in anhydrous DMF (1 ml) and reaction was stirred at room temperature overnight. HPLC showed mostly cyclized triphosphate (~82%). Reaction mixture was concentrated and residue was washed with anhydrous diethyl ether 3×. It was redissolved in anhydrous DMF and concentrated to dryness on rotavap. Residue was taken with DDAO-monophosphate, ammonium salt (5 mg, 1.5 eq.) in 200 μl anhydrous DMF and stirred at 40° C. over the weekend. HPLC showed formation of a new product with desired UV characteristics at 11.96 min. (HPLC Method: 0.30% acetonitrile in 0.1 M triethylammonium acetate (pH 7) in 15 min, and 30–50% acetonitrile in 5 min, Novapak C-18 3.9×150 mm column, 1 ml/min). LCMS (ES−) also showed a major mass peak 834 for M−1 peak. Reaction mixture was concentrated and purified on Deltapak C18, 19×300 mm column using 0.1 M TEAB (pH 6.7) and acetonitrile. Fraction with product was repurified by HPLC using the same method as described above. Fraction with pure product was concentrated, coevaporated with MeOH (2×) and water (1×). Residue was dissolved in water (1.2 ml) to give a 1.23 mM solution. HPCL purity as 254 nm>97.5%, at 455 nm>96%; UV $\lambda_A$=267 nm and 455 nm; MS: M−1=834.04 (calc 8.33.95).

δ-9H(1,3-dichloro-9,9-dimethylacridin-2-one-7=yl)-dideoxycytidine-5'-tetraphosphate (ddC4P-DDAO), δ-9H(1,3-dichloro-9,9-dimethylacridin-2-one-dideoxyadenosine-5'-tetraphosphate (ddA4P-DDAO) and δ-9H(1,3-dichloro-9,9-dimethylacridin-2-one-y-YL)-dideoxyguanosine-5'-tetraphosphate (ddG4P-DDAO) were synthesized and purified in a similar fashion. Analysis of these purified compounds provided the following data: ddC4P-DDAO: UV$\lambda_A$=268 nm and 454 nm; MS: M−1=819.32 (calc 818.96); ddA4P-DDAO: UV$\lambda_A$=263 nm and 457 nm; MS: M−1=843.30 (calc 842.97); ddG4P-DDAO: UV$\lambda_A$=257 nm and 457 m; MS: M−1=859.40 (calc 858.97).

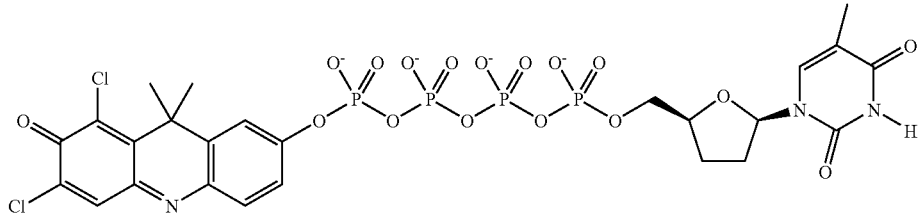

ddT4P-DDAO

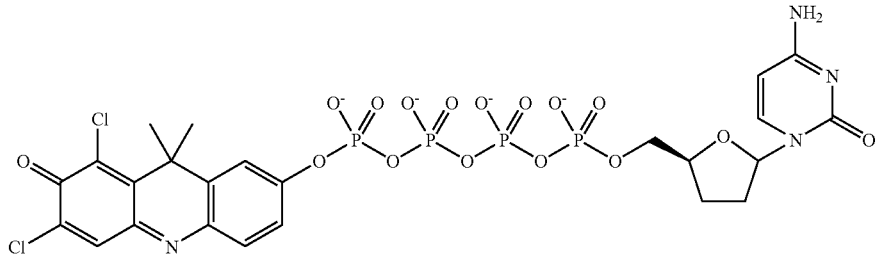

ddC4P-DDAO

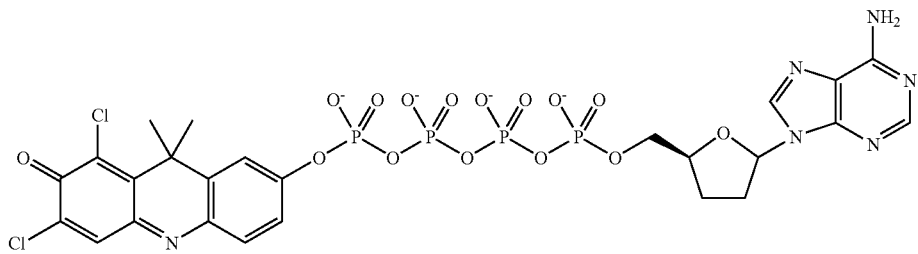

ddA4P-DDAO

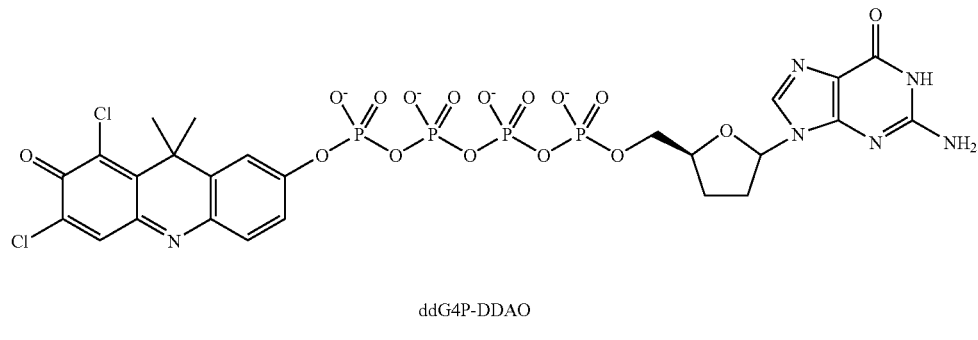

ddG4P-DDAO

Example 4

Preparation of ε-9H (1,3-dichloro-9,9-dimethylacridin-2-one-7-yl)-dideoxythymidine-5'-pentaphosphate DDAO-ddT-pentaphosphate (ddT5P-DDAO)

A. Preparation of DDAO Pyrophosphate

DDAO-phosphate diammonium salt (11.8 μmol) was coevaporated with anhydrous DMF (3×0.25 ml) and was dissolved in DMF (0.5 ml). To this carbonyldiimidazole (CDI, 9.6 mg, 5 eq) was added and the mixture was stirred at room temperature overnight. Excess CDI was destroyed by addition of MeOH (5 μl) and stirring for 30 minutes. To the mixture tributylammoniumdihydrogen phosphate (10 eq., 236 ml of 0.5 M solution in DMF) was added and the mixture was stirred at room temperature for 4 days. Reaction mixture was concentrated on rotavap. Residue was purified on HiPrep 16.10 Q XL column using 0–100% B using 0.1 M TEAB/acetonitrle (3:1) as buffer A and 1 M TEAB/acetonitrile (3:1) as buffer B. Main peak (HPLC purity 98%) was collected, concentrated and coevaporated with methanol (2×). Residue was dissolved in 1 ml water to give 5.9 mM solution. UV/VIS$\lambda_{max}$=456 nm.

B. Preparation of ddT5P-DDAO ddTTP (100 μl of 47.5 mM solution in water) was coevaporated with anhydrous DMF (2×1 ml). To this DCC (5 eq., 4.9 mg) was added and mixture was coevaporated with DMF (1×1 ml). Residue was taken in anhydrous DMF (0.5 ml) and stirred at room temperature for 3 hours. To this 1.03 eq of DDAO pyrophosphate, separately coevaporated with anhydrous DMF (2×1 ml) was added as a DMF solution. Mixture was concentrated to dryness and then taken in 200 μl anhydrous DMF. Mixture was heated at 38° C. for 2 days. Reaction mixture was concentrated, diluted with water, filtered and purified on HiTrap 5 ml ion exchange column using 0–100% A–B using a two step gradient. Solvent A=0.1 M TEAB/acetonitrile (3:1) and solvent B=1 M TEAB/acetonitrile (3:1). Fraction 12 and 13 which contained majority of product were combined, concentrated and coevaporated with methanol (2×). Residue was repurified on Xterra RP C-18 30–100 mm column using 0.30% acetonitrile in 0.1 M TEAB in 5 column and 30–50% acetonitrile in 2 column volumes, flow rate 10 ml/min. Fraction containing pure product was concentrated and coevaporated with methanol (2×) and water (1×). HPLC purity at 455 nm>99%. UV/VIS=268 nm and 455 nm. MS: M−1=914.03 (calc 913.93).

The DDAO dye attached to the gamma phosphate of these polyphosphates is fluorescent with an excitation maximum of 455 nm and an emission maximum of about 608 nm. Upon hydrolysis of the phosphate ester to release the free dye, the spectrum changes with excitation maximum of about 645 nm and emission maximum of about 659 nm. The change is readily detected by simple fluorescence measurements or color change.

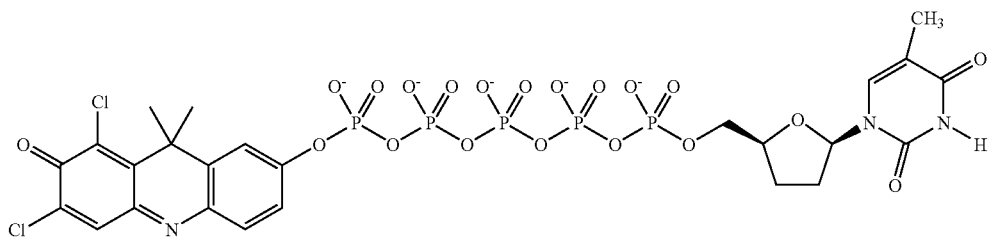

ddT5P-DDAO

Example 5

Preparation of δ-9H(1,3-dichloro-9,9-dimethylacridin-2-one-7-yl)-deoxythymidine-5'-tetraphosphate (dT4P-DDAO)

10 μmoles TTP TEA salt was evaporated to dryness. To the residue was added 40 μmoles tributylamine and 5 ml dry pyridine. The solution was re-evaporated to dryness. After 2 coevaporations with 3 ml dry dimethylformamide (DMF), residue was re-dissolved in 200 μl dry DMF, flushed with argon and stoppered. Using a syringe, 50 μmoles (8 mg)

carbonyldiimidazole (CDI) dissolved in 100 μl dry DMF was added. The flask was stirred for 4 hr at ambient temperature.

While the above reaction was progressing, 35 mg (83 μmoles) DDAO phosphate and 166 μmoles tributylamine were dissolved in dry DMF. The DDAO phosphate was evaporated to dryness followed by 3 coevaporations with dry DMF. Residue was dissolved in 300 μl dry DMF.

After the 4 hr reaction time, 3.2 μl anhydrous methanol was added to the TTP-CDI reaction. The reaction was stirred 30 minutes. To this mixture, DDAO phosphate solution was added and mixture was stirred at ambient temperature for 18 hr. The reaction was checked by Reverse phase HPLC (Xterra 4.6×100 column, 0.1 M TEAA/acetonitrile). The reaction volume was reduced to 200 μl by evaporation and the reaction was allowed to progress for 80 hr.

After 80 hr, the reaction was stopped by adding 15 ml 0.1 M TEAB. The diluted mixture was applied to a 19×100 Xterra RP column and eluted with an acetonitrile gradient in 0.1 M TEAB. The fractions containing pure T4P-DDAO were evaporated to dryness and coevaporated twice with ethanol. The residue was reconstituted with MilliQ water. Yield: 1.10 μmole, 11%; HPLC purity>98% at 455 nm; MS: M−1=850.07 (calc. 849.95)

δ-9H(1,3-dichloro-9,9-dimethylacridin-2-one-7-yl)-deoxyguanosine-5'-tetraphosphate (dG4P-DDAO), δ-9H(1,3-dichloro-9,9-dimethylacridin-2-one-7-yl)-deoxycytidine-5'-tetraphosphate (dC4P-DDAO) and δ-9H(1,3-dichloro-9,9-dimethylacridin-2-one-7-yl)-deoxyadenosine-5'-tetraphosphate (dA4P-DDAO) were prepared in a similar manner as described above except 3.5 equivalents of DDAO phosphate was used instead of 8.3 equivalents. After C18 purification, samples were purified on ion exchange using a Mono Q 10/10 column.

δ-9H(1,3-dichloro-9,9-dimethylacridin-2-one-7-yl)-deoxyguanosine-5'-tetraphosphate (dG4P-DDAO): Yield 0.57 μmol, 5.7%; HPLC purity 99% at 455 nm; MS: M−1=875.03 (calc. 874.96).

δ-9H(1,3-dichloro-9,9-dimethylacridin-2-one-7-yl)-deoxycytidine-5'-tetraphosphate (dC4P-DDAO): Yield 0.24 μmole, 2.4%; HPLC purity 99% at 455 nm; MS: M−1=835.03 (calc. 834.95).

δ-9H(1,3-dichloro-9,9-dimethylacridin-2-one-7-yl)-deoxyadenosine-5'-tetraphosphate (dA4P-DDAO): Yield 0.38 μmole, 3.8%; HPLC purity 99% at 455 nm; MS: M−1=859.07 (calc. 858.97).

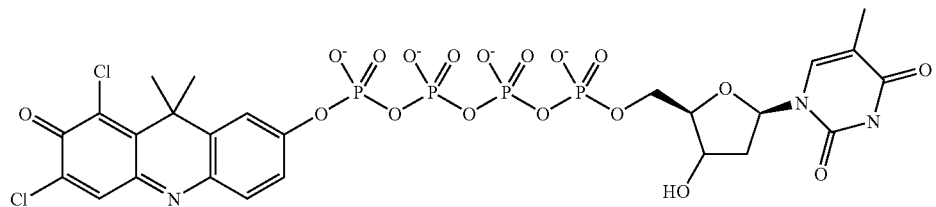

dT4P-DDAO

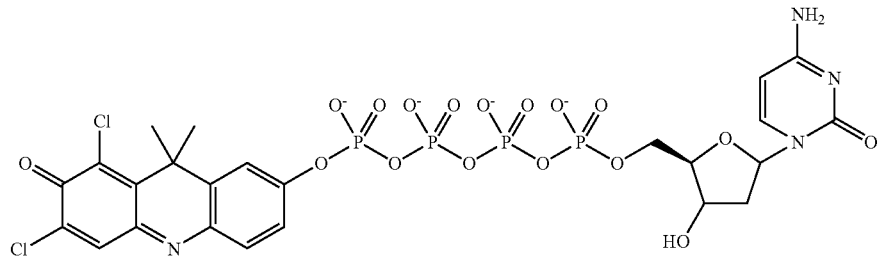

dC4P-DDAO

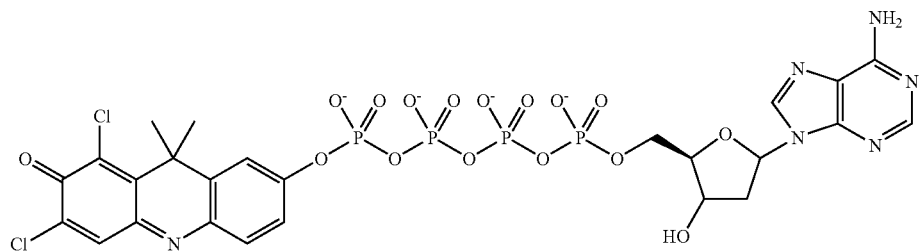

dA4P-DDAO

-continued

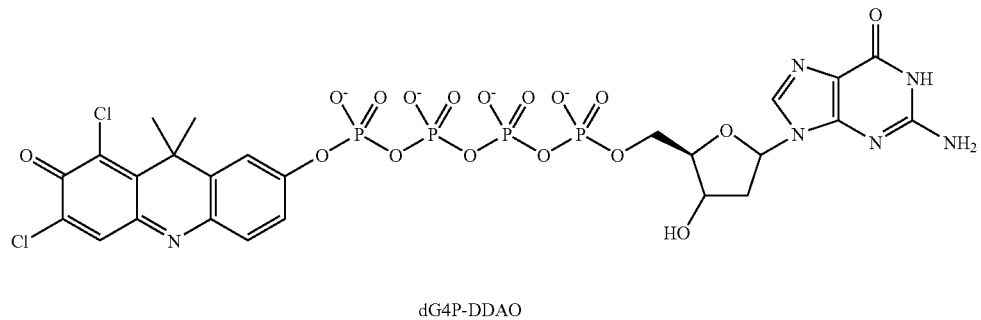

dG4P-DDAO

Example 6

Figure 2:
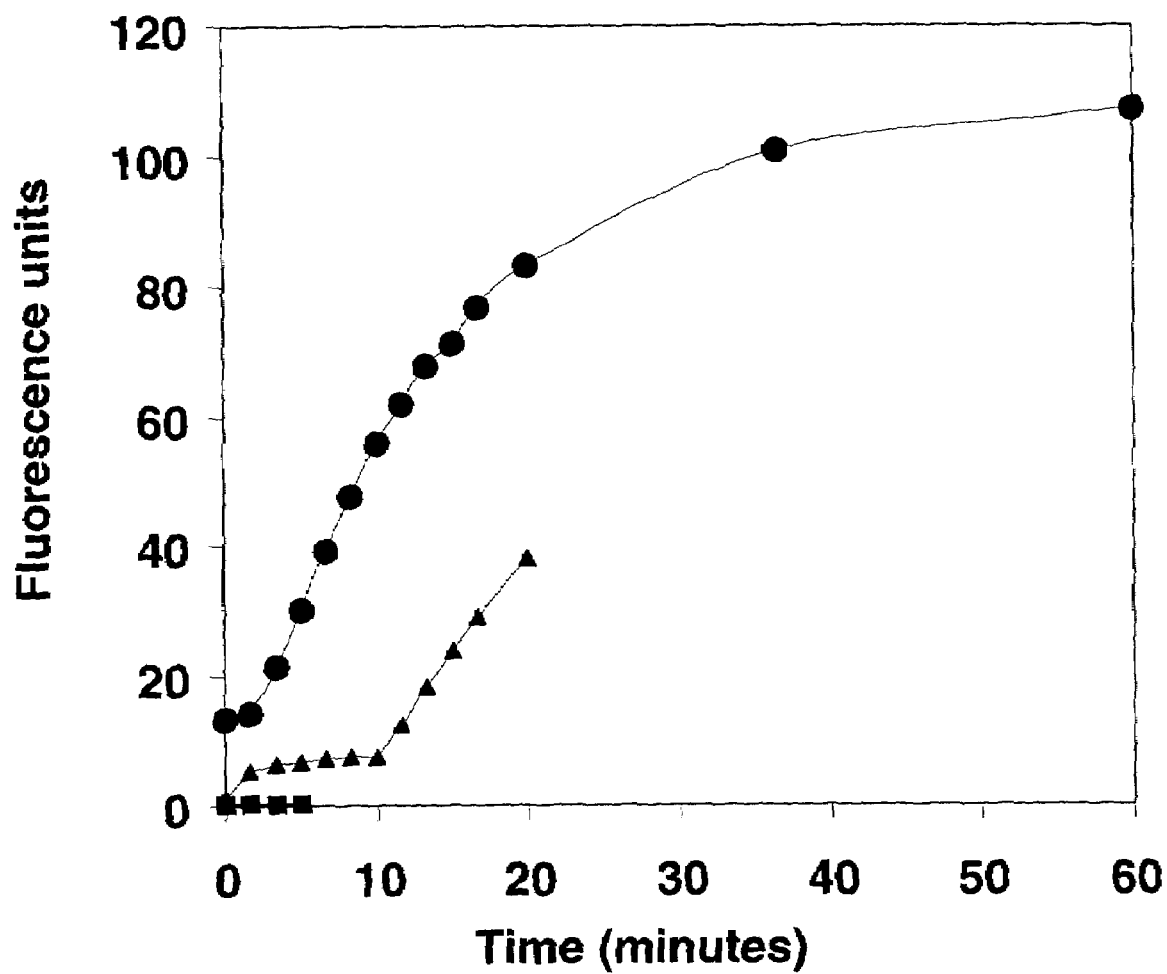
FIG. 2 is a graph of time versus fluorescence emission obtained by the use of a 5'→3' exonuclease to amplify signal generated by incorporation of nucleotides labeled on the terminal phosphate with fluorogenic dyes.

Use of Exonuclease III to Amplify Signal Generated by Incorporation of Nucleotides Labeled on the Terminal Phosphate with Fluorogenic Dyes A 50 μl reaction containing 25 mM Tris HCl, pH 8.05 mM MgCl$_2$, 0.5 mM MnSO$_4$, 40 pmoles ddT4P-DDAO (DDAO-δ-2',3'-dideoxythymidine-5'-tetraphosphate), 5 pmoles primer (5'GTTTTCCCAGTCACGACGTTGT*A3' (SEQ ID NO: 1) where * is phosphorothioate linkage) and 10 pmoles template (5'GTCGTTATACAACGTCGTGACTGGGAAAA*ddC3' (SEQ ID NO: 2) where * is phosphorothioate linkage, ddC indicates a terminal dideoxynucleotide) was annealed by heating to 75° for 4 minutes and cooled to 21° C. Referring now to FIG. 2, to this reaction was added the following: 0.15 units shrimp alkaline phosphatase and 0.5 units exonuclease III (squares) or 0.15 units shrimp alkaline phosphatase, 0.5 units exonuclease III, and 16 units Thermo Sequenase (circles). To a third reaction mixture, 0.15 units shrimp alkaline phosphatase and 16 units Thermo Sequenase were added, then after 10 minutes, 0.5 units exonuclease III was added (triangles). Reactions were incubated at room temperature in a quartz fluorescence ultra-microcuvet in an LS-55 Luminescence Spectrophotometer (Perkin Elmer), operated in time drive mode with excitation at 612 nm and emission at 670 nm. Emission is displayed in arbitrary units.

As shown in FIG. 2, no fluorescence emission was obtained from the reaction mixture without polymerase. Moreover, as shown in FIG. 2, amplification of the signal is only obtained when both exonuclease III and polymerase are present in the reaction mixture.

Example 7

Figure 3:
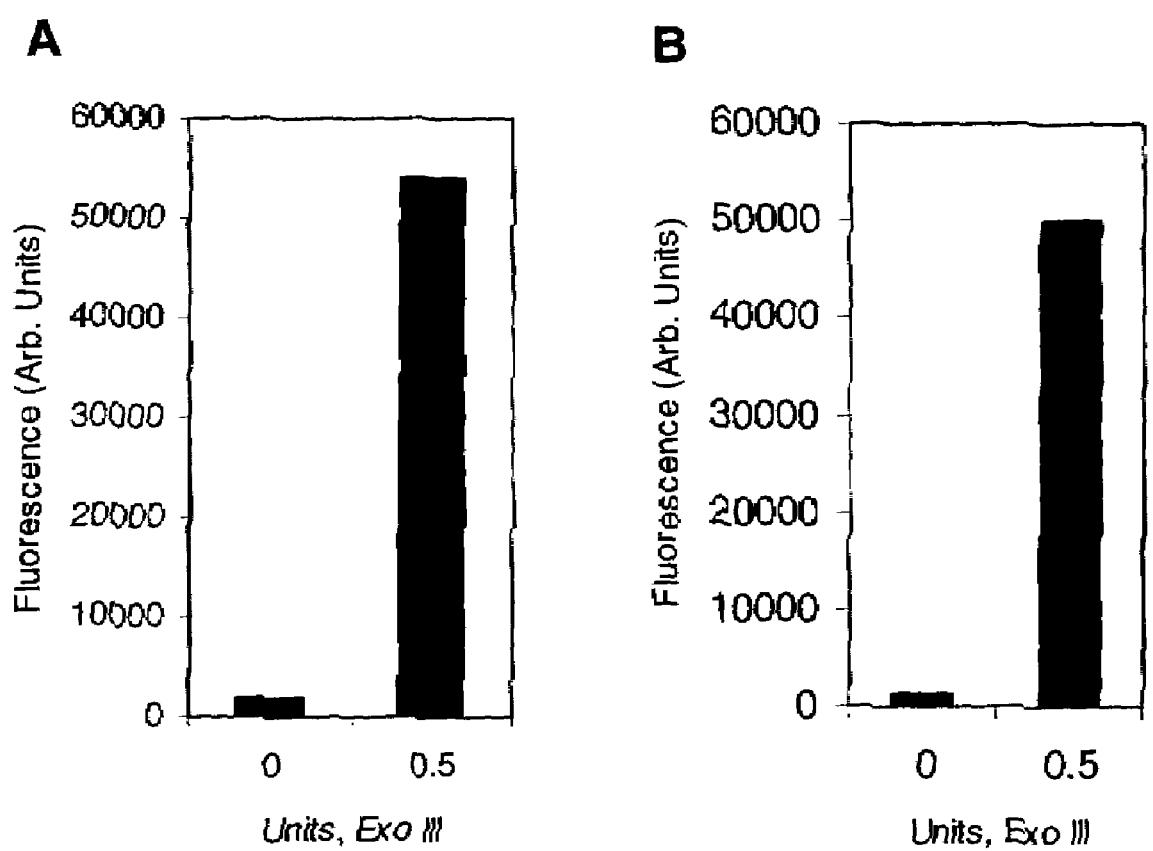
FIGS. 3(A and B) shows bar graphs of the fluorescence emission obtained by the use of a 5'→3' exonuclease to amplify signal generated by the sequence specific incorporation of nucleotides labeled on the terminal phosphate with fluorogenic dyes.

Use of Exonuclease III to Amplify Signal Generated by the Sequence Specific Incorporation of Nucleotides Labeled on the Terminal Phosphate with Fluorogenic Dyes with Sequence Specificity With reference to FIG. 3A, an assay was performed to determine the presence of deoxycytidine (C) in the template. For each result shown in FIG. 3A, a 50 μl reaction containing 25 mM Tris HCl, pH 8.0, 5 mM MgCl$_2$, 0.5 mM MnSO$_4$, 40 pmoles of ddG3P-resorufin (resorufin-γ-2',3'-dideoxyguanosine-5'-triphosphate), 5 pmoles primer (5'GTTTTCCCAGTCACGACGTTGT*A3' (SEQ ID NO: 1) where * is phosphorothioate linkage) and 10 pmoles template (5'GTCGTTCTACAACGTCGTGACTGGGAAAA*ddC3' (SEQ ID NO: 3) where * is phosphorothioate linkage, and ddC indicates a terminal dideoxynucleotide) was annealed by heating to 75° C. for 4 minutes and cooled to 21° C. Thus, for FIG. 3A the primer/template combination was:

```
5' GTTTTCCCAGTCACGACGTTGTA           (SEQ ID NO: 1)

ddCAAAAGGGTCAGTGCTGCAACATCTTGCTG    (SEQ ID NO: 3)
```

To this, 0.15 units shrimp alkaline phosphatase and 16 units Thermo Sequenase DNA polymerase were added, with exonuclease III added as indicated. The reaction was incubated at 21° C. for 40 minutes. After incubation, 25 μl was removed to a 96 well plate and fluorescence was measured in a Tecan ULTRA plate reader with 530 nm excitation and 590 nm emission filters. Fluorescence emission is displayed in arbitrary units.

With reference now to FIG. 3B, an assay was performed to determine the presence of deoxythymidine (T) in the template. For each result shown in FIG. 3B, a 50 μl reaction containing 25 mM Tris HCl, pH 8.0, 5 mM MgCl$_2$, 0.5 mM MnSO$_4$, 40 pmoles of ddT4P-DDAO (DDAO-δ-2',3'-dideoxythymidine-5'-tetraphosphate), 5 pmoles primer (5'GTTTTCCCAGTCACGACGTTGT*A3' (SEQ ID NO: 1) where * is phosphorothioate linkage) and 10 pmoles template (5'GTCGTTATACAACGTCGTGACTGGGAAAA*ddC3' (SEQ ID NO: 2) where * is phosphorothioate linkage, and ddC indicates a terminal dideoxynucleotide) was annealed by heating to 75° C. for 4 minutes and cooled to 21° C. Thus, the primer/template combination was:

```
5' GTTTTCCCAGTCACGACGTTGTA           (SEQ ID NO: 1)

ddCAAAAGGGTCAGTGCTGCAACATATTGCTG    (SEQ ID NO: 2)
```

To this, 0.15 units shrimp alkaline phosphatase and 16 units Thermo Sequenase DNA polymerase were added, with exonuclease III added as indicated. The reaction was incubated at 21° C. for 40 minutes. After incubation, 25 μl was removed to a 96 well plate and fluorescence was measured in a Tecan ULTRA plate reader with 612 nm excitation and 670 nm emission filters. Fluorescence emission is displayed in arbitrary units.

As shown in FIG. 3A, for reactions containing the terminal-phosphate-labeled dideoxyguanosine triphosphate dye, fluorescence emission was detected for the Primer-Template combination where the next nucleotide in the template was a dC. With reference to FIG. 3B, for reactions containing the terminal-phosphate-labeled dideoxythymidine tetraphosphate, fluorescence emission was detected for the Primer-Template combination where the next nucleotide in the template was a dA. Cleavage of the pyrophosphate product of phosphoryl transfer by shrimp alkaline phosphatase leads to a detectable change in the resorufin or DDAO label which allows for the detection of the nucleic acid, the synthesis and degradation of the complementary labeled nucleotide being repeated several times to effect the amplification of the signal.

Example 8

Detection of Streptavidin Derivatized Beads Using a Biotinylated Oligo and ddA4P-methylcoumarin A. Attachment of Biotinylated Oligo to Streptavidin Derivatized Beads.

Streptavidin coated beads (100 μl, 10 mg/ml) were washed with 1×PBS-Tween (0.01%) 225 μl and 1×PBS, 225 μl. Beads were incubated with a mixture of 195 μl PBS-Tween (0.01%) and 5 μl of 50 μM solution of a biotinylated oligo (capable of forming a hairpin at 37° C., SEQ ID NO: 4 at 37° C. for 30 min. After separation of supernatent, beads were washed with 0.5 ml PBS-Tween (0.01%), 0.5 ml of PBS buffer and resuspended in 0.5 ml PBS buffer. Oligo loading was determined to be 9 pmol/500 μl of the final bead suspension, after cleavage of oligo from a portion of the beads with conc. NH4OH at 65° C. for 10 min and measuring the fluorescence of fluorescein attached to the oligo.

(50 μl) and reaction buffer (50 μl, 25 mM Hepes, pH 8.2, 5 mM MgCl2, 0.5 mM MnCl2, 0.01% Tween-20, 0.0026 u/μl shrimp alkaline phosphatase, 1 mM DTT, 4.76 μM dA4P-methylcoumarin, 4.76 μM dG4P-methylcoumarin, 4.76 μM dC4P-methylcoumarin, 4.76 μM T4P-methylcoumarin, 0.065 u/μl Exo III and 0.012 u/μl TSI polymerase). Beads were incubated in the same reaction buffer at 37° C. for 1.5 h. Supernatent was separated and fluorescence was measured on Tecan ULTRA with excitation at 360 nm and emission at 465 nm. About 27% of starting dN4P-methylcoumarin nucleotides (257.7 pmol) were consumed giving an ~286 fold amplification of signal.

Example 10

Detection of Streptavidin Derivatized Beads Using a Biotinylated Oligo and Three Methylcoumarin Labeled Nucleotides (dA4P-methylcoumarin, dG4P-methylcoumarin, dC4P-methylcoumarin) and a DDAO Labeled Nucleotide (T4P-DDAO)

50 μl of oligo-loaded beads per example 8A were separated from the supernatant and washed with deionized water

SEQ ID NO: 4

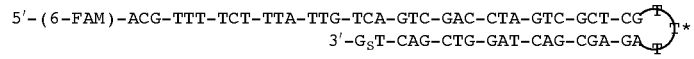

Where T* is a biotinylated thymidine base and s stands for phosphorothioate backbone that is resistant to Exo-III.

B. Detection of Streptavidin Derivatized Beads Using ddA4P-methylcoumarin by Repeated Addition and Removal of ddAMP to the Biotinylated Oligo.

50 μl of the oligo loaded beads (0.9 pmol oligo) were separated from the supernatant and washed with deionized water (50 μl) and reaction buffer (50 μl, 25 mM Hepes, pH 8.2, 5 mM MgCl2, 0.5 mM MnCl2, 0.01% Tween-20, 0.0026 u/μl shrimp alkaline phosphatase, 1 mM DTT, 5 μM ddA4P-methylcoumarin, 0.065 u/μl Exo III and 0.012 u/μl TSI polymerase). Beads were incubated in the same reaction buffer at 37° C. for 1.5 h. Supernatent was separated and fluorescence was measured on Tecan ULTRA plate reader with excitation at 360 nm and emission at 465 nm. About 81% of starting ddA4P-methylcoumarin (202.6 pmol) was consumed giving an ~225 fold amplification of signal.

Example 9

Detection of Streptavidin Derivatized Beads Using a Biotinylated Oligo and All Four dN4P-methylcoumarin Nucleotides (N=A,G,C & T)

50 μl of oligo-loaded beads per example 8A were separated from the supernatant and washed with deionized water (50 μl) and reaction buffer (50 μl, 25 mM Hepes, pH 8.2, 5 mM MgCl2, 0.5 mM MnCl2, 0.01% Tween-20, 0.0026 u/μl shrimp alkaline phosphatase, 1 mM DTT, 4.76 μM dA4P-methylcoumarin, 4.76 μM dG4P-methylcoumarin, 4.76 μM dC4P-methylcoumarin, 4.76 μM T4P-DDAO and 0.012 u/μl TSI polymerase). No Exo III was used. Beads were incubated in the same reaction buffer at 37° C. for 1.5 h. Supernatent was separated and fluorescence was measured on Tecan ULTRA with excitation at 360 nm and emission at 465 nm for methylcoumarin and excitation at 612 nm and emission at 670 nm for DDAO. Ratio of methylcoumarin and DDAO fluorescence counts was 7.1–7.4 very close to the expected value of 7.0 (ratio of the sum of A,G & C to T bases when the sequence is fully extended) indicating that sequence composition may be used to differentiate one analyte signal from another.

Having described the particular, desired embodiments of the invention herein, it should be appreciated that modifications may be made therethrough without departing from the contemplated scope of the invention. The true scope of the invention is set forth in the claims appended hereto.

What is claimed is:

1. A method of detecting an analyte comprising the steps of:
   (a) anchoring said analyte to a nucleic acid template;
   (b) conducting a nucleic acid polymerase reaction to produce labeled inorganic polyphosphate by-product, said reaction comprising the reaction of said template, a primer, at least one terminal phosphate-labeled nucleotide, and a nucleic acid polymerase; and
   (c) analyzing said labeled polyphosphate.

2. The method of claim 1, wherein said primer is a nuclease resistant primer.

3. The method of claim 2, wherein the nucleic acid polymerase reaction further includes an enzyme having 3'→5' exonuclease activity.

4. The method of claim 1, wherein said analyzing step includes (a) reacting said labeled polyphosphate with a phosphatase to produce a detectable species characteristic of said analyte and (b) detecting said detectable species.

5. The method of claim 1, further including the step of separating any nucleic acid template not anchored by said analyte before said conducting step.

6. The method of claim 4, wherein said at least one terminal phosphate-labeled nucleotide is substantially non-reactive to phosphatase, further wherein said reacting step and said conducting step are carried out simultaneously.

7. The method of claim 1, further comprising the step of characterizing said analyte.

8. The method of claim 7, further comprising the step of quantifying said analyte.

9. The method of claim 1, wherein said analyte is DNA, RNA, protein, lipid, oligosaccharide, a whole cell, or a synthetic polymer.

10. The method of claim 1, wherein said analyte is anchored to said nucleic acid template by non-covalent binding, or by one or more covalent bonds.

11. The method of claim 1, wherein said nucleic acid polymerase is a DNA polymerase or an RNA polymerase.

12. The method of claim 2, wherein said nuclease resistant primer includes a methyl phosphonate, a borano phosphate or a phosphorothioate linkage.

13. The method of claim 1, wherein said nucleic acid template and said primer are switched and it is said primer that is anchored to the analyte.

14. The method of claim 1, wherein said nucleic acid template and said primer are part of a DNA hairpin, and said DNA hairpin is anchored to said analyte in said anchoring step.

15. The method of claim 4, wherein said detectable species is detectable by a property selected from the group consisting of color, fluorescence emission, chemiluminescence, mass change, oxidation/reduction potential and combinations thereof.

16. The method of claim 4, wherein said detectable species is produced in amounts substantially proportional to the amount of analyte.

17. The method of claim 1, wherein at least one terminal phosphate-labeled nucleotide includes four or more phosphate groups in the polyphosphate chain.

18. The method of claim 1, wherein the labels in at least one terminal phosphate-labeled nucleotide are enzyme-activatable labels selected from the group consisting of chemiluminescent compounds, fluorogenic dyes, chromogenic dyes, mass tags, electrochemical tags and combinations thereof.

19. The method of claim 1, wherein said terminal phosphate-labeled nucleotides carry distinct labels.

20. The method of claim 19, wherein the presence of an analyte is determined by the ratio of distinct labels produced.

21. The method of claim 1, wherein one or more additional detection reagents are added in said polymerase reaction of said conducting step, and said additional detection reagents are capable of a response that is detectably different from said labeled polyphosphate.

22. The method of claim 1, wherein at least one terminal phosphate-labeled nucleotides are deoxy nucleotides and carry different labels.

23. The method of claim 1, wherein at least one terminal-phosphate-labeled nucleotide is represented by the formula:

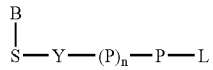

wherein P is phosphate (PO$_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; and P-L is a phosphorylated label which preferably becomes independently detectable when the phosphate is removed.

24. The method of claim 23, wherein said sugar moiety is selected from the group consisting of ribosyl, 2'-deoxyribosyl, 3'-deoxyribosyl, 2', 3'-dideoxyribosyl, 2', 3'-didehydrodideoxyribosyl, 2'-alkoxyribosyl, 2-azidoribosyl, 2-aminoribosyl, 2'-fluororibosyl, 2'-mercaptoriboxyl, 2'-alkylthioribosyl, carbocyclic, acyclic and other modified sugars.

25. The method of claim 23, wherein said base is selected from the group consisting of uracil, thymine, cytosine, guanine, 7-deazaguanine, hypoxanthine, 7-deazahypoxanthine, adenine, 7-deazaadenine, 2,6-diaminopurine and analogs thereof.

26. The method of claim 23, wherein said enzyme-activatable label is selected from the group consisting of chemiluminescent compounds, fluorogenic dyes, chromogenic dyes, mass tags, electrochemical tags and combinations thereof.

27. The method of claim 26, wherein said enzyme-activatable label is a fluorogenic moiety selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacirdin-2-one-7-yl phosphate, 6,8-difluoro-4-methylumbelliferyl phosphate, and derivatives thereof.

28. The method of claim 26, wherein said phosphorylated label is a chromogenic moiety selected from the group consisting of 5-bromo-4-chloro-3-indolyl phosphate, 3-indoxyl phosphate, p-nitrophenyl phosphate, and derivatives thereof.

29. The method of claim 26, wherein said chemiluminescent compound is an alkaline phosphatase-activated 1,2-dioxetane compound.

30. The method of claim 29, wherein said 1,2-dioxetane compound is selected from the group consisting of 2-chloro-5-(4-methoxyspiro[1,2-dioxetane-3,2'-(5-chloro-)tricyclo[3,3,1-1$^{3,7}$]-decan]-1-yl)-1-phenyl phosphate, chloroadamant-2'-ylidenemethoxyphenoxy phosphorylated dioxetane, 3-(2'-spiroadamantane)-4-methoxy-4-(3"-phosphoryloxy)phenyl-1,2-dioxetane and derivatives thereof.

31. A method of detecting and characterizing multiple analytes in a sample, comprising the steps of:
(a) anchoring to each analyte a specific template nucleic acid sequence with a unique base at the site opposite to the complementary nucleotide being added;
(b) conducting a DNA polymerase reaction to produce labeled inorganic polyphosphate by-product, said reaction comprising the reaction of said templates, primers complementary to said specific template sequence, two or more terminal phosphate-labeled nucleotides with different labels, a DNA polymerase and an enzyme having 3'→5' exonuclease activity;
(c) permitting said labeled polyphosphates to react with a phosphatase to produce detectable species unique to each of said analytes; and
(d) detecting said detectable species.

32. A method of detecting and characterizing multiple analytes in a sample, comprising the steps of:
(a) anchoring to each analyte a specific template nucleic acid sequence with a unique base at the site opposite to the complementary nucleotide being added;
(b) conducting a DNA polymerase reaction to produce uniquely labeled inorganic polyphosphate by-product; said reaction comprising the reaction of said templates, nuclease resistant primers complementary to said specific target sequence of each of said multiple analytes, two or more terminal phosphate-labeled nucleotides having 4 or more phosphate groups in the polyphosphate chain and each bearing a different label, a DNA polymerase and an enzyme having 3'→5' exonuclease activity; and (c) detecting the labeled polyphosphates.

33. A method of detecting and characterizing multiple analytes in a reaction compartment, comprising the steps of:
   (a) anchoring a unique template nucleic acid sequence to each of said analytes;
   (b) anchoring said analytes to the surface of said reaction compartment;
   (c) conducting a DNA polymerase reaction to produce labeled inorganic polyphosphate by-product; said reaction comprising the reaction of the unique template sequence of one of said analytes, a nuclease resistant primer complementary to said unique template sequence, at least one terminal phosphate-labeled nucleotides having 4 or more phosphate groups in the polyphosphate chain, a DNA polymerase and an enzyme having 3'→5' exonuclease activity;
   (d) detecting said labeled polyphosphate;
   (e) washing off the unanchored components; and
   (f) repeating steps (a) to (d) with a nuclease resistant primer complementary to another unique template sequence of a different analyte until all the analytes are analyzed.

34. The method of claim 33, wherein said detecting step includes:
   (a) permitting said labeled polyphosphate to react with a phosphatase to produce a detectable species; and
   (b) detecting said detectable species.

* * * * *